US012599417B2

(12) United States Patent
Bennett et al.

(10) Patent No.: US 12,599,417 B2
(45) Date of Patent: Apr. 14, 2026

(54) PATELLA BONE PLATE SYSTEMS

(71) Applicants: Smith & Nephew, Inc., Memphis, TN (US); Smith & Nephew Orthopaedics AG, Zug (CH); Smith & Nephew Asia Pacific PTE. Limited, Singapore (SG)

(72) Inventors: Charles R. Bennett, Memphis, TN (US); Gabriel E. Rapalo, Arlington, TN (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/711,737

(22) PCT Filed: Jan. 17, 2023

(86) PCT No.: PCT/US2023/010892
§ 371 (c)(1),
(2) Date: May 20, 2024

(87) PCT Pub. No.: WO2023/137216
PCT Pub. Date: Jul. 20, 2023

(65) Prior Publication Data
US 2025/0009400 A1 Jan. 9, 2025

Related U.S. Application Data

(60) Provisional application No. 63/300,086, filed on Jan. 17, 2022.

(51) Int. Cl.
*A61B 17/80* (2006.01)

(52) U.S. Cl.
CPC ...... *A61B 17/8061* (2013.01); *A61B 17/8052* (2013.01); *A61B 17/8085* (2013.01)

(58) Field of Classification Search
CPC .................................................. A61B 17/8061
See application file for complete search history.

(56) References Cited

U.S. PATENT DOCUMENTS

| | | | |
|---|---|---|---|
| 2013/0053899 A1* | 2/2013 | Bluechel | ............ A61B 17/8061 |
| | | | 606/281 |
| 2017/0065315 A1 | 3/2017 | Helfet | |
| 2020/0078061 A1 | 3/2020 | Penman | |

FOREIGN PATENT DOCUMENTS

| | | |
|---|---|---|
| CN | 201631362 | 11/2010 |
| CN | 214966501 | 12/2021 |
| CN | 215425030 | 1/2022 |

OTHER PUBLICATIONS

Arthrex Inc., "Patella Fracture System," Arthrex.com, Surgical Technique, 20 pages (2016).
(Continued)

*Primary Examiner* — Andrew Yang
(74) *Attorney, Agent, or Firm* — KDW Firm PLLC

(57) ABSTRACT

Disclosed are examples of a patella bone plate. In some examples, the patella bone plates may include a contoured body with a longitudinal axis, and with a radius of curvature, a plurality of contoured arms and extending superiorly from the contoured body, the plurality of contoured arms spaced apart from the longitudinal axis, the plurality of contoured arms, a plurality of holes, a hook, the hook having a radius of curvature configured to allow the hook to extend around an apex of the patella, a hole located on the hook, the hole defining a distal fixation screw path that is substantially parallel to and offset from the longitudinal axis. In various examples, the contoured body may have a single arm with a staggered hole arrangement. The plurality of holes may
(Continued)

include variable angle holes, locking holes, fixation holes, slots, or a combination thereof.

19 Claims, 13 Drawing Sheets

(56)               References Cited

OTHER PUBLICATIONS

Depuy Synthes, "2.4/2.7 MM Variable Angle Locking Lateral Rim Patella Plates: Variable Angle Locking Patella Plating System," Surgical Technique, 32 pages (2022).
International Search Report for International Application No. PCT/US2023/010892, mailed May 22, 2023, 15 pages.
Konigsee Implantate, "Product Overview: Implants," Konigsee Implantate GmbH, Edition 09: 33 pages (Nov. 2019).
Wild et al., "Variable Angle-Stable Patella-Plate," Konigsee Implantate GmbH, 16 pages, (Aug. 2013).

* cited by examiner

113

111

103

125

104

119

111

PATELLA BONE PLATE SYSTEMS

CROSS-REFERENCE TO RELATED APPLICATIONS

This application is a National Phase filing of International Application No. PCT/US2023/010892, filed Jan. 17, 2023, which application claims the benefit of U.S. Provisional Patent Application Ser. No. 63/300,086, filed Jan. 17, 2022, and titled "Patella Bone Plate Systems," the entire contents of each application is hereby incorporated by reference.

TECHNICAL FIELD

The present disclosure is directed to orthopedic implants for coupling to one or more patient's bones, bone portions, bone fragments, etc., and orthopedic surgical methods for implanting such orthopedic implants, and, more specifically, to bone plate systems and surgical techniques for facilitating stabilization of patella fractures.

BACKGROUND

The patella is a small sesamoid bone located at the knee joint, connected to the femur via the quadriceps tendon and connected to the tibia via the patellar tendon. A properly functioning patella slides within a groove located on the distal femur as the knee joint moves between extension and flexion, helping to guide the relative movements of the femur and the tibia. When a patella fracture occurs, it presents a significant challenge to a surgeon. The patella is subject to high forces and has articulating surfaces that should not be interfered with during a repair. Also, the small size of the patella and the relative softness of patella bone makes coupling hardware to the patella difficult.

In general, patella fractures have typically been treated with tension band wiring, sutures, cerclage wire, and plates and screws, or a combination of such treatments. Bone plate fixation is a preferred method of patella fracture fixation due to its stability and rigidity. Conventional bone plate fixation techniques operate only on the anterior portion of the patella. However, full and secure compression of the fracture is difficult using only anterior approaches. Therefore, it would be desirable to have a bone plate or other fixation technique that allowed a surgeon to compress a patella fracture on the distal portion of the patella (for example, alone or in combination with anterior compression). It is with this in mind that the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein are improved devices and techniques, in particular, for patellar fracture repair procedures. In any preceding or subsequent example, a device may be in the form of a patella bone plate. In any preceding or subsequent example, a patella bone plate may have an anterior portion configured to be arranged on an anterior portion of the patella and a hook portion configured to be arranged on or around a distal end (for instance, an apex) of the patella and to extend up along a posterior portion of the patella. In various examples, the hook portion may include an opening configured to receive a fastener to couple the patella bone plate to a distal end of the patella.

In any preceding or subsequent example, a patella bone plate may include a contoured body configured to extend along a longitudinal axis of at least a portion of an anterior portion of a patella, the longitudinal axis may extend from a base to an apex of the patella; and a hook portion configured to be arranged around the apex of the patella and extend a distance along a posterior portion of the patella.

In any preceding or subsequent example of the patella bone plate, the patella bone plate may further include a distal opening arranged in the hook.

In any preceding or subsequent example of the patella bone plate, the distal opening may be configured to receive a distal fastener for coupling the patella bone plate to a distal end of the patella.

In any preceding or subsequent example of the patella bone plate, the distal opening may provide a fixation screw path for the distal fastener from the apex to a base of the patella.

In any preceding or subsequent example of the patella bone plate, the fixation screw path may be offset from a longitudinal axis of the contoured body.

In any preceding or subsequent example of the patella bone plate, the fixation screw path may be configured to allow the distal fastener to avoid interference from body fasteners configured to couple at least a portion of the contoured body to the patella.

In any preceding or subsequent example of the patella bone plate, the distance along the inferior portion of the patella is about 1 mm to about 10 mm.

In any preceding or subsequent example of the patella bone plate, the patella bone plate may further include a plurality of openings arranged in the contoured body, each of the plurality of openings may be configured to receive a fastener for coupling the patella bone plate to a portion of the patella.

In any preceding or subsequent example of the patella bone plate, the plurality of openings may be arranged in a staggered pattern.

In any preceding or subsequent example of the patella bone plate, the contoured body may include a superior end portion and an inferior end portion, wherein the superior end portion is formed as a pair of arms extending from the inferior end portion.

In any preceding or subsequent example of the patella bone plate, the contoured body may have a radius of curvature corresponding to a radius of curvature of the anterior portion of a patella.

In any preceding or subsequent example of the patella bone plate, the hook may have a radius of curvature corresponding to at least a portion of a radius of curvature of the apex.

In any preceding or subsequent example of the patella bone plate, the hook may have a radius of curvature configured to allow the hook to extend around the axis and contact the posterior portion of the patella.

In any preceding or subsequent example of the patella bone plate, the hook may be configured to be inserted through a split patellar tendon of the patella.

In any preceding or subsequent example of the patella bone plate, the patella bone plate may further include a peripheral portion coupled to the contoured body to form a mesh.

In any preceding or subsequent example of the patella bone plate, the patella bone plate may further include a plurality of openings in the mesh configured to receive fasteners for coupling the mesh to the anterior portion of the patella, the plurality of openings may include about 15 openings to about 25 openings.

In any preceding or subsequent example of the patella bone plate, the mesh may be configured to cover about 30% to about 50% of an area of the anterior portion.

In any preceding or subsequent example of the patella bone plate, the mesh may include a medial-superior segment, a medial-inferior segment, a lateral-inferior segment, and a lateral-superior segment.

In any preceding or subsequent example of the patella bone plate, the mesh may include the contoured body integrally formed with the peripheral portion.

In any preceding or subsequent example, a method of treating a patella fracture using a patella bone plate may include implanting the patella bone plate on the patella via: arranging a contoured body of the patella adjacent to an anterior portion of the patella, the contoured body configured to extend along a longitudinal axis of at least a portion of an anterior portion of a patella, the longitudinal axis extending from a base to an apex of the patella; and arranging a hook portion of the patella bone plate around an axis of the patella, the hook portion configured to be arranged around the apex of the patella and extend a distance along a posterior portion of the patella.

In any preceding or subsequent example of the method, the method may further include splitting the patellar tendon of the patella, and inserting the hook portion through a split patellar tendon.

In any preceding or subsequent example of the method, the hook portion may include a distal opening arranged in the hook portion.

In any preceding or subsequent example of the method, the method may include coupling the hook portion to a distal end of the patella via installing a distal fastener through the distal opening.

In any preceding or subsequent example of the method, the distal opening may provide a fixation screw path for the distal fastener from the apex to a base of the patella.

In any preceding or subsequent example of the method, the fixation screw path may be offset from a longitudinal axis of the contoured body.

In any preceding or subsequent example of the method, the fixation screw path may be configured to allow the distal fastener to avoid interference from body fasteners configured to couple at least a portion of the contoured body to the patella.

In any preceding or subsequent example of the method, the distance along the inferior portion of the patella may be about 1 mm to about 10 mm.

In any preceding or subsequent example of the method, the contoured body may include a plurality of openings arranged, each of the plurality of openings configured to receive a fastener for coupling the patella bone plate to a portion of the patella.

In any preceding or subsequent example of the method, the plurality of openings may be arranged in a staggered pattern.

In any preceding or subsequent example of the method, the contoured body may include a superior end portion and an inferior end portion, the superior end portion may be formed as a pair of arms extending from the inferior end portion.

In any preceding or subsequent example of the method, the contoured body may have a radius of curvature corresponding to a radius of curvature of the anterior portion of a patella.

In any preceding or subsequent example of the method, the hook portion may have a radius of curvature corresponding to at least a portion of a radius of curvature of the apex.

In any preceding or subsequent example of the method, the hook portion may have a radius of curvature configured to allow the hook portion to extend around the axis and contact the posterior portion of the patella.

In any preceding or subsequent example of the method, the patella bone plate may include a peripheral portion coupled to the contoured body to form a mesh.

In any preceding or subsequent example of the method, the mesh may include a plurality of openings configured to receive fasteners for coupling the mesh to the anterior portion of the patella, the plurality of openings comprising about 15 openings to about 25 openings.

In any preceding or subsequent example of the method, the mesh may be configured to cover about 30% to about 50% of an area of the anterior portion.

In any preceding or subsequent example of the method, the mesh may include a medial-superior segment, a medial-inferior segment, a lateral-inferior segment, and a lateral-superior segment.

In any preceding or subsequent example of the method, the mesh may include the contoured body integrally formed with the peripheral portion.

In any preceding or subsequent example, a patella bone plate may include a contoured body with a longitudinal axis, a first length, a superior end portion and an inferior end portion, the contoured body having an interior surface and an outer surface opposite the inner surface, the contoured body having a radius of curvature of R1, a plurality of contoured arms with a second length and extending superiorly from the contoured body at the superior end portion, the plurality of contoured arms spaced apart from the longitudinal axis, the plurality of contoured arms having an interior surface and an outer surface opposite the inner surface, the contoured arms having a radius of curvature of R1, a plurality of holes spaced along the first length of the contoured body and the second length of the plurality of contoured arms, the plurality of holes extending from the interior surface to the outer surface, a hook at the inferior end portion of the contoured body, the hook having an interior surface configured to contact a central distal surface of the patella, an outer surface opposite the interior surface, the hook having a radius of curvature of R2, a hole extending from the outer surface of the hook to the interior surface, the hole defining a distal fixation screw path that is substantially parallel to and offset from the longitudinal axis and a distal paddle extending in a superior direction from the hook.

In any preceding or subsequent example, a patella bone plate may include a contoured body with a longitudinal axis, a medial-lateral axis, a length, a superior end portion and an inferior end portion, the contoured body having an interior surface and an outer surface opposite the inner surface, the contoured body having a radius of curvature of R3, a plurality of holes spaced along the length of the contoured body, the plurality of holes offset from the central longitudinal axis, the plurality of holes also offset from each other about the medial-lateral axis, and extending from the interior surface to the outer surface, a hook at the inferior end portion of the contoured body, the hook having an interior surface configured to contact a central distal surface of the patella, and an outer surface opposite the interior surface, the hook having a radius of curvature of R4, a hole extending from the outer surface of the hook to the interior surface, the hole defining a distal fixation screw path that is substantially parallel to, and offset from the longitudinal axis and a distal paddle extending in a superior direction from the hook.

In any preceding or subsequent example, a meshed patella bone plate may include a contoured body with a central longitudinal axis, a medial-lateral axis, a length, a superior end portion and an inferior end portion, the contoured body having an interior surface and an outer surface opposite the interior surface, the contoured body having a radius of curvature, a plurality of holes spaced along the length of the contoured body, each of the plurality of holes offset from the central longitudinal axis, the plurality of holes also offset from each other about the medial-lateral axis, and extending from the interior surface to the outer surface, a hook at the inferior end portion of the contoured body, the hook having an interior surface configured to contact a central distal surface of the patella, and an outer surface opposite the inner surface, the hook having a radius of curvature, a hole extending from the outer surface of the hook to the interior surface, the hole defining a screw path that is substantially parallel to, and offset from the longitudinal axis, a distal paddle extending in a superior direction from the hook, a peripheral portion integrally formed with the contoured body, the peripheral portion having an interior surface and an outer surface opposite the inner surface, the peripheral portion having a radius of curvature, the peripheral portion further comprising a superior-medial segment, an inferior-medial segment, an inferior-lateral segment and a superior-lateral segment, the superior-medial segment and superior-lateral segment combining with the contoured body at the superior end portion, the inferior-medial segment and the inferior-lateral segment combining with the contoured body at the inferior end portion, the superior-medial segment and the inferior-medial segment combining at a medial end of the peripheral portion, the superior-lateral segment and the inferior-lateral segment combining at a lateral end of the peripheral portion and a plurality of holes spaced along the peripheral portion, each of the plurality of holes extending from the interior surface to the outer surface.

In any preceding or subsequent example, the plurality of holes may comprise variable angle holes, locking holes, fixation holes, slots, or a combination thereof. In any preceding or subsequent example, the variable angle holes may comprise a series of fins arranged about the inner surface of the hole. The fins may be arranged to provide screw fixation including and up to and around 15 degrees about an axis formed perpendicular to the top and bottom surfaces of the plate. Additionally, the screw fixation angles may vary, depending on the location of the holes on the plate and on the orientation of the fins relative to the top and bottom surfaces of the plate. In any preceding or subsequent example, the plurality of holes may be positioned along the outer periphery surface of the plate, or they may be centrally located (e.g., positioned closer or substantially adjacent to the central longitudinal axis of the contoured body). Any threaded locking screw holes may be sized and configured to receive, for example, 2.7 mm locking screws. The variable angled holes may be sized and configured to receive, for example, 2.7 mm bone screws. Alternatively, in any preceding or subsequent example, any threaded locking screw holes and the variable angled fastener holes may be the same size. For instance, in any preceding or subsequent example, the threaded locking screw holes and the variable angled fastener holes may be sized and configured to receive, for example, 2.7 mm bone screws.

In any preceding or subsequent example, the plate may be made of titanium, stainless steel, a polymer and combinations thereof. The plate may be bendable by a user using hand tools or it may be provided more rigid. Additionally, the plate may be provided with suture holes and/or hardware for attaching an orthopedic cerclage cable or sutures.

In any preceding or subsequent example, a surgical method for patella fracture repair, comprising making an incision adjacent the patella, reducing a patella fracture using a fracture reduction aid, placing a patella bone plate on the patella, splitting a patellar tendon attached to the patella, inserting a hook end of a patella bone plate through the patellar tendon, reducing the patella fracture using bone fixators, and optionally securing the patella bone plate with a proximally extending bone screw. Fluoroscopy may be used to verify screw path placement during drilling of the screws in the plate to prevent joint penetration. Additionally, the reduction aids may be K-wires and/or reduction forceps. In further examples, parts of patella bone plate or mesh may be bent as needed by the surgeon to achieve a better fit to the anterior side of the patella. Fluoroscopy may also be used to confirm patella bone plate or mesh position.

Examples of the present disclosure provide numerous technological advantages over conventional devices and techniques. For instance, in one non-limiting example of a technological advantage, the features of patella bone plates of the present disclosure improve the surgeon's ability to fix the majority of the patella fractures needing open reduction internal fixation. Locked plating in the patella has already been proven to be superior to standard treatments. The addition of variable angle locking along with fracture compression by the plate may improve the mechanical stability of the fracture fixation. In another non-limiting technological advantage, patella bone plates may include a hook configured to be arranged around a distal end of a patella and extend up along a portion of the posterior side of the patella. Accordingly, patella bone plates according to any preceding or subsequent example may provide for support of both the anterior and superior side of the patella. In an additional non-limiting technological advantage, patella bone plates may include a distal opening configured to allow a fastener to be arranged through the distal end (e.g., the apex) of the patella. Patella bone plates according to any preceding or subsequent example are capable of supporting a fracture of a patella in a more effective manner than conventional devices and techniques, allowing surgical teams to have easier implantation techniques, less post-surgery complications, and, therefore, improved patient outcomes.

Further features and advantages of at least some of the examples of the present disclosure, as well as the structure and operation of various examples of the present disclosure, are described in detail below with reference to the accompanying drawings.

BRIEF DESCRIPTION OF THE DRAWINGS

By way of example, specific examples of the disclosed device will now be described, with reference to the accompanying drawings, in which.

Figure 1:
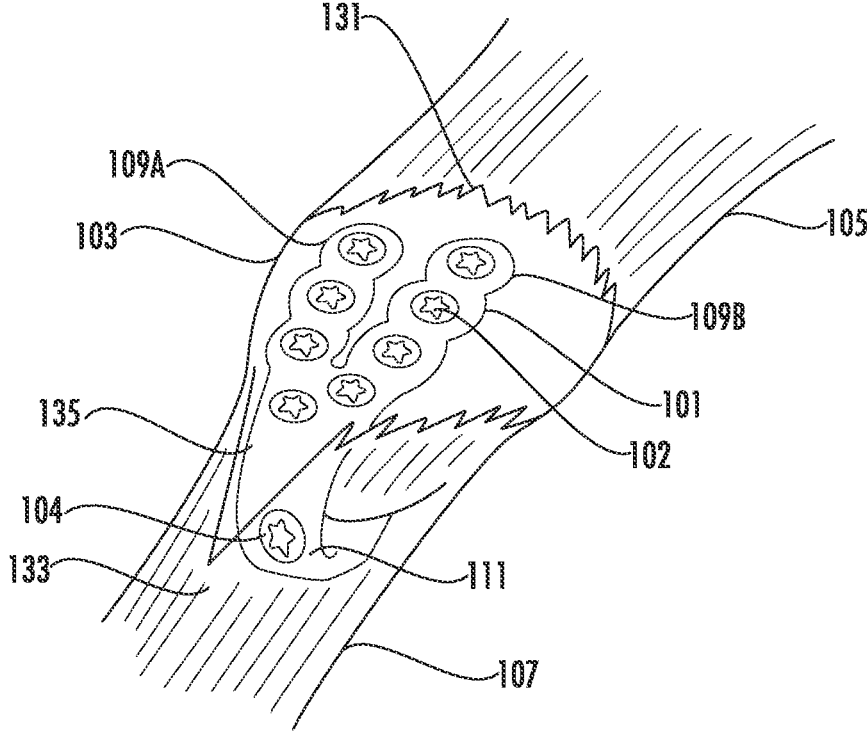
FIG. 1 is a perspective view of a dual-armed or Y-shaped patella bone plate located on a patella in accordance with one or more features of the present disclosure.

It should be understood that the drawings are not necessarily to scale and that the disclosed examples are sometimes illustrated diagrammatically and in partial views. In certain instances, details which are not necessary for an understanding of the disclosed methods and devices or which render other details difficult to perceive may have been omitted. It should be further understood that this disclosure is not limited to the particular examples illustrated herein.

DETAILED DESCRIPTION

Various features of patella bone plates will now be described more fully hereinafter with reference to the accompanying drawings, in which one or more features of the patella bone plates will be shown and described. It should be appreciated that the various features may be used independently of, or in combination, with each other. It will be appreciated that a patella bone plate as disclosed herein may be embodied in many different forms and should not be construed as being limited to the examples set forth herein. Rather, these examples are provided so that the present disclosure will convey certain features of the patella bone plate to those skilled in the art. In the drawings, like numbers refer to like elements throughout unless otherwise noted.

Disclosed herein are patella bone plates including one or more features for enabling increased fixator placement when coupling the plates to a patient's patella. For example, patella bone plates according to various examples may be configured to, among other things, lock the bone and plate dorsally through the plate using a combination of plate contours and variable angle screw trajectories by splitting the patellar tendon. Every year, numerous patients undergo surgery to address a fractured patella. However, patellar fractures pose unique challenges. For example, the posterior side of the patella has a layer of articular cartilage. The posterior surface of the patella is shaped to glide smoothly over the trochlea of the femur. If any repair hardware, such as screws, sutures, wires, and/or the like were to interfere with this surface, it would be very painful for the patient. For instance, in one scenario, improper placement of a single bone screw may cause the bone screw to poke through the posterior side of the patella and violate the articular cartilage.

The patella is typically about 25 millimeters (mm) at its thickest point from the anterior side to the posterior side. In addition, the patella is connected at its superior portion and its inferior portion to two thick tendons, the quadriceps tendon and the patellar tendon. These two tendons may further complicate securement and positioning of a plate, fasteners, and/or other hardware to the patient's bone. Additionally, the quadriceps muscle can exert large forces on the patella, further complicating treatment. As a result, conventional techniques for treating patellar fractures are generally difficult and provide limited options.

Accordingly, the present disclosure provides various patella bone plates including one or more features that may be used in combination or singularly to provide increased flexibility, control, and precision in enabling a surgeon to position and secure a patella bone plate across a fracture in a patient's patella, thereby increasing procedure success rates and patient outcomes.

Patella bone plates described according to examples in the present disclosure may have various shapes and/or configurations. It should be appreciated that the patella bone plates may be provided in any suitable shape and/or configuration, which will be appreciated by one of ordinary skill in the art. For example, a patella bone plate may include a bone conforming arcuate surface.

In addition, a patella bone plate according to some examples may include any now known or hereafter developed additional features such as, for example, one or more openings or slots designed to receive, for instance, surgical implantation tools like Kirschner wires (or K-wires), reduction forceps, different fasteners (e.g., non-locking fasteners), and/or the like.

Patella bone plates according to some examples may be manufactured from any suitable material now known or hereafter developed, including, for example, metals, polymers, plastics, ceramics, resorbable, non-resorbable, composite materials, etc. Suitable materials may include, for example, titanium, stainless steel, cobalt chrome, polyetheretherketone (PEEK), polyethylene, ultra-high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a patient's body. In some examples, the bone fastener may be manufactured from the same material as the patella bone plate. In other examples, the fasteners may be manufactured from a different material as compared to the patella bone plate.

The fastener can be any type of fastener now known or hereafter developed. For example, the fastener may include any type of external thread including standard or non-standard threads. For instance, the external threads can be arranged as a continuous ridge or a non-continuous ridge. The external threads can form a portion of a revolution, one complete revolution, multiple revolutions, a single lead, multiple leads, or any other threads known in the art. Additionally, and/or alternatively, in the case of locking screws, the head portion of the fastener can include any surface that will engage with and seat within a locking screw opening formed in the bone fixation plates. For example, the head portion can include threads. In various examples, the head portion can include a series of dimples, ridges, bumps, textured areas, or any other surface that can operate to secure or further secure the fastener.

The fastener may be any fastener now known or hereafter developed, made out of any appropriate material now known or hereafter developed. The fastener may include a bore for receiving a driver in order to drive the fastener through the patella bone plate and into the patient's bone. The bore may be any size and shape, for example, it may have a hexagonal configuration to receive a corresponding hexagonal driver, a Phillips screw head, a flat-head, a star configuration, Torx, or any other appropriate configuration that can cooperate with a driver to drive the fastener through the plate and into the patient's bone.

The shaft of the fastener may be fully threaded, partially threaded, or a helical blade, and/or may include one or more tacks, deployable talons, expandable elements, or any feature that allows the shaft to engage the patient's bone. It is also possible that shaft be non-threaded so that the fastener takes the form of a peg or a pin. This alternative implementation may be preferred in certain procedures where, for instance, the main goal is to prevent tilting of a bone segment or in procedures where there is no concern of the fastener pulling out from the patient's bone and hence no need for the shaft to be threaded or otherwise configured to engage the patient's bone. The end of the shaft may be a self-tapping or self-drilling tip.

Patella bone plates according to various examples may include one or more features arranged and configured to provide improved fixation of the patella bone plate to a patella while minimizing, reducing, or even eliminating damage to the patella. In various examples, patella bone plates may be arranged and configured to provide improved fixation at the inferior surface and/or anterior portion of the patella while preserving the patella tendon function. Thus, it should be appreciated that the present disclosure should not be limited to any particular configuration of patella bone plate having any particular configuration unless specifically claimed.

Referring to FIGS. 1-8, various examples of a dual-armed or Y-shaped patella bone plate 101 are disclosed. As shown in FIG. 1, patella bone plate 101 may be arranged, implanted, installed, or otherwise coupled to a patient's patella 103. Patella 103 has a base 131 and an apex 133 (e.g., the inferior border of the patella 103). In turn, patella 103 is connected to a quadriceps tendon 105 at the base 131 and to a patellar tendon 107 at the apex 133.

Figure 6:
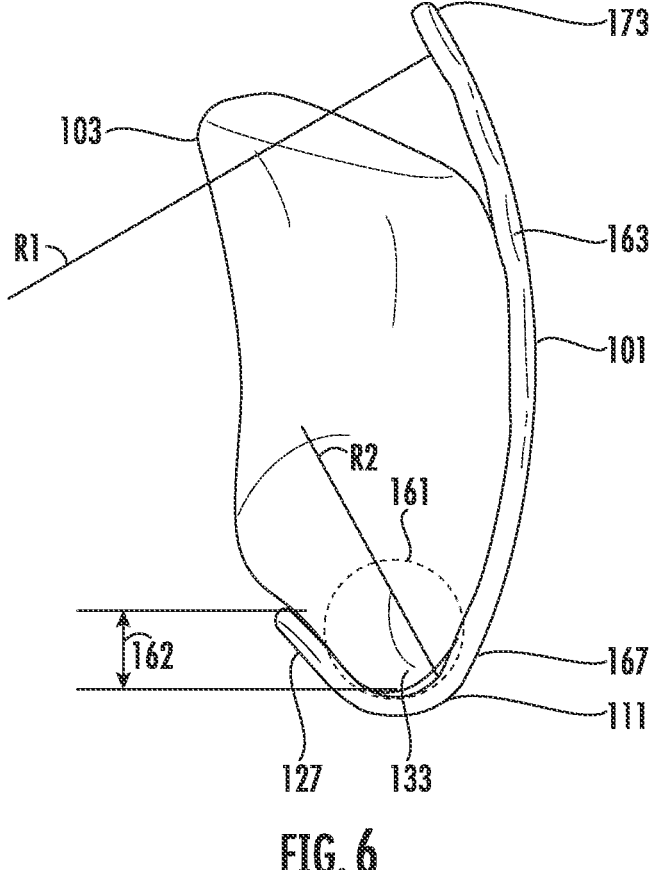
FIG. 6 is an additional side view of the dual-armed patella bone plate shown in FIG. 1, showing the radii of curvature of the patella bone plate.

Patella bone plate 101 may include a contoured body 163 with a superior end portion 165, an inferior end portion 167, and a longitudinal axis 171. As shown in FIG. 6, at least a portion of contoured body 163 may be contoured or otherwise shaped to correspond to the shape of an anterior portion of the patella 103. For example, a portion of contoured body 163 that contacts the anterior portion of the patella 103 may be shaped (or may be bent by a surgeon to be shaped) to correspond with the anterior portion of the patella 103. Longitudinal axis 171 extends along a longitudinal length of the patella 103 (i.e., a length extending from the base 131 to the apex 133)

At the superior end portion 165, contoured arms 109*a* and 109*b* meet contoured body 163, and extend superiorly from superior end portion 165, and are also offset from longitudinal axis 171. Patella bone plate 101 may further include a hook (hook portion, apex portion, distal end portion) 111, located adjacent inferior end portion 167. In various examples, during an implantation procedure, patellar tendon 107 may be split at 135 to accommodate hook 111. As previously discussed, patella bone plate 101 may be secured to the patella 103 with a variety of bone screws 102. Bone screws 102 may help reduce a variety of fractures in the patella. Advantageously, a distal hole 104 may be located at the bottom of the patella bone plate 101 and provide for additional fixation at or near the apex 133 of the patella, for example, for fracture reduction.

In various examples, hook 111 may be configured to extend around the apex 133 to a back or posterior side of the patella. Accordingly, patella bone plate 101 may have a portion that may be arranged adjacent to and/or coupled to the front or anterior side of the patella 103 and a portion that may be arranged adjacent to and/or coupled to the back or posterior side (and/or the apex or distal end) of the patella 103. Referring to FIG. 6, a back or posterior portion 127 of hook 111 may extend a distance 162 up the posterior side of the patella 103. In some examples, distance 162 may be about 1 mm, about 3 mm, about 5 mm, about 10 mm, about 15 mm, about 20 mm, about 25 mm, and any value or range between any two of these values (including endpoints). In some examples, one or more openings 113 may be arranged in back or posterior portion 127 (for example, at or near a paddle 119) of hook 111, for instance, to allow a fastener to be passed through the distal portion and into the posterior portion of the patella.

Patella bone plate 101 may also have a number of cutouts 125. Cutouts 125 may be or may include notches or areas of the patella bone plate 101 where material has been removed from the patella bone plate 101. The notches or removal of material makes the patella bone plate 101 easier to bend or contour. This allows the patella bone plate 101 to be contoured to more closely match a particular patient's anatomy and reduces the amount of foreign material in the patient. In general, a contoured portion includes a bent or curved portion, for example, curved to correspond to a portion of patient anatomy.

Figure 2:
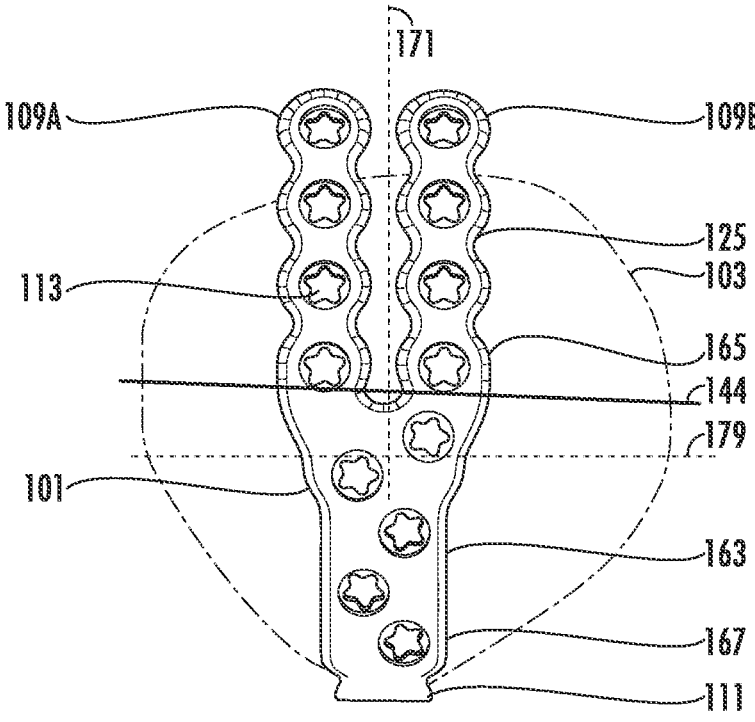
FIG. 2 is a front view of the dual-armed patella bone plate shown in FIG. 1.
Figure 3:
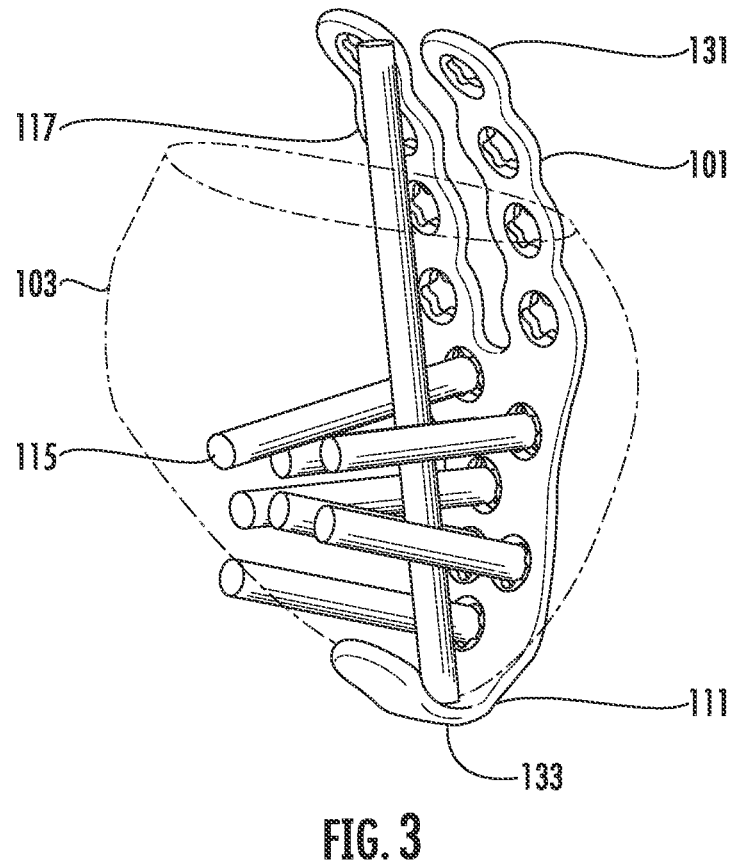
FIG. 3 is a side view of the dual-armed patella bone plate shown in FIG. 1, showing screw fixation angles.
Figure 4:
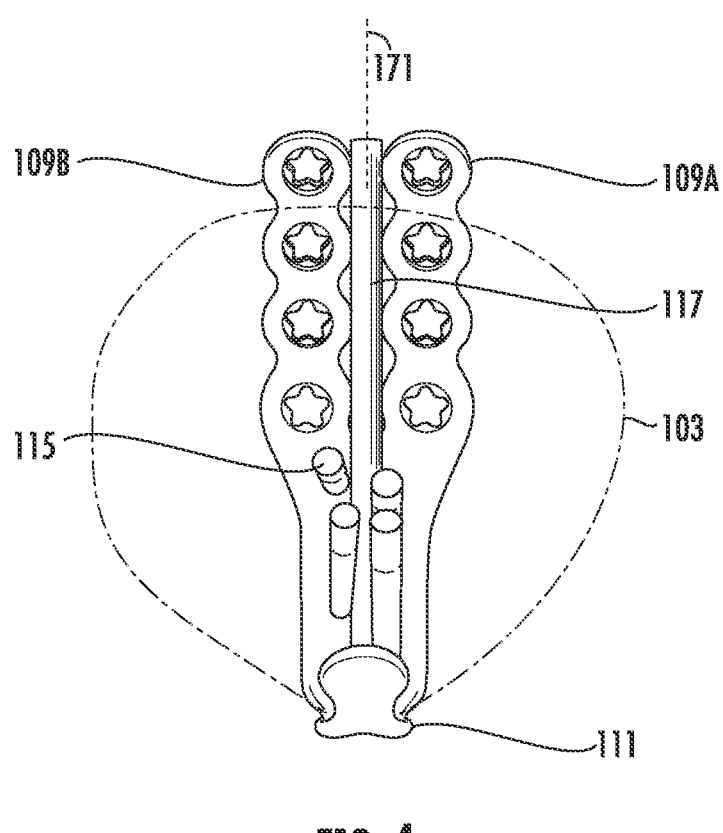
FIG. 4 is a rear view of the dual-armed patella bone plate shown in FIG. 1, showing screw fixation angles.

FIG. 2 illustrates the example shown in FIG. 1, but without showing the soft tissue. Patella bone plate 101 has a plurality of openings 113. In the example shown in FIG. 2 and as previously discussed, openings 113 may allow for fastener fixation. In some examples, a fastener may include, without limitation, a screw, a variable angle screw, and/or the like.

One non-limiting advantage of examples of patella bone plates according to the present disclosure is the ability of the described patella bone plates to capture and support different types of patella fractures. The fracture 144 shown in FIG. 2 is a simple frontal/coronal fracture, but the ability to reduce other types of fractures, including, without limitation, sagittal, lateral, sagittal, medial, frontal/coronal, wedge, and/or the like are all within the scope of the present disclosure.

In the example shown in FIG. 2, each arm portion 109 has four openings 113, although a greater or lesser number of openings may be used. In the example depicted in FIG. 2, the contoured body 163 has five openings 113, although a greater or lesser number of openings 113 may be used. Openings 113 are arranged in an offset pattern in FIG. 2. However, openings 113 of contoured body 163 may also be staggered about medial-lateral axis 179, or arranged to be parallel to the longitudinal axis 171. In some examples, patella bone plate 101 may have various numbers of openings arranged in various different patterns.

In some examples, openings 113 may be in the form of a locking screw (or fastener) opening or a variable angled opening or variable angled fastener (or screw) opening (terms used interchangeably herein without the intent to limit). That is, as will be appreciated by one of ordinary skill in the art, openings 113 may include a plurality of threads formed on an inner surface thereof for mating with threads formed on an outer surface of a head portion of a bone fastener. Thus arranged, the bone fastener may be said to be locked to the patella bone plate 101, 121, 151 via the openings 113. That is, as will be appreciated by one of ordinary skill in the art, the bone fastener is threaded through one of the openings 113 formed in the patella bone plate 101, 121, 151 and into the patient's bone. The bone fastener is secured to the patella bone plate 101, 121, 151 via threads formed on the head portion of the bone fastener that cooperate with openings 113 formed in the patella bone plate 101, 121, 151. This secures the patella bone plate 101, 121, 151 with respect to the patient's bone and provides rigid fixation between the patella bone plate 101, 121, 151 and the bone fasteners. That is, because the head portion of the bone fastener interdigitates with the threads formed in the openings 113 of the patella bone plate 101, 121, 151, the patella bone plate 101, 121, 151 and the fasteners form a stable system or construct, and the stability of the fracture can be dependent on or aided by the stiffness of the construct. Locking a bone fastener into the patella bone plate 101, 121, 151 can achieve angular and axial stability and reduce or even completely eliminate the possibility for the bone fastener to vibrate, toggle, slide, dislodge, or otherwise move, thereby reducing the risk of postoperative loss of reduction.

In some examples, the patella bone plate 101, 121, 151 may include a plurality of openings 113 formed therein for receiving a fastener, such as a non-locking or variable angled (e.g., polyaxial) bone fastener. In various examples, the openings 113 may be arranged and configured to enable the bone screws inserted therein (for example, 102 in FIG. 1) to achieve a greater range of insertion angles as compared to, for example, a conventional locking screw that is threadably coupled to the patella bone plate 101, 121, 151. For example, the angular position of the bone fastener may be rotated through a rotation range, for instance, a range of approximately ±15 degrees, although the range of allowable polyaxial rotation can vary, including greater and less than ±15 degrees. In some examples, the openings 113 may be provided in any suitable manner, configuration, etc. now known or hereafter developed for enabling polyaxial positioning or angling of the bone fastener relative to the patella bone plate 101, 121, 151.

In various examples, the openings 113 may include fins or projections that extend radially inward from an inner surface of the openings 113 and into an interior region of the openings 113, and which are configured to engage or cooperate with the head portion of the bone fastener. In some examples, the fins engage the head portion of the bone fastener in order to secure the bone fastener at a desired position and at a desired angular orientation within the opening 113. Non-limiting examples of the operation and configuration of the fins can be found in U.S. patent application Ser. No. 15/706,877, with an earliest filing date of Jul. 25, 2005, now U.S. Pat. No. 10,092,337 entitled "Systems and Methods for Using Polyaxial Plates"; U.S. patent application Ser. No. 13/524,506, filed on Jun. 15, 2012, entitled "Variable Angle Locking Implant", and International PCT Patent Application No. PCT/US20/35729, filed on Jun. 2, 2020, entitled "Orthopedic Implant with Improved Variable Angle Locking Mechanism", the entire contents of which are hereby incorporated by reference.

Figure 5:
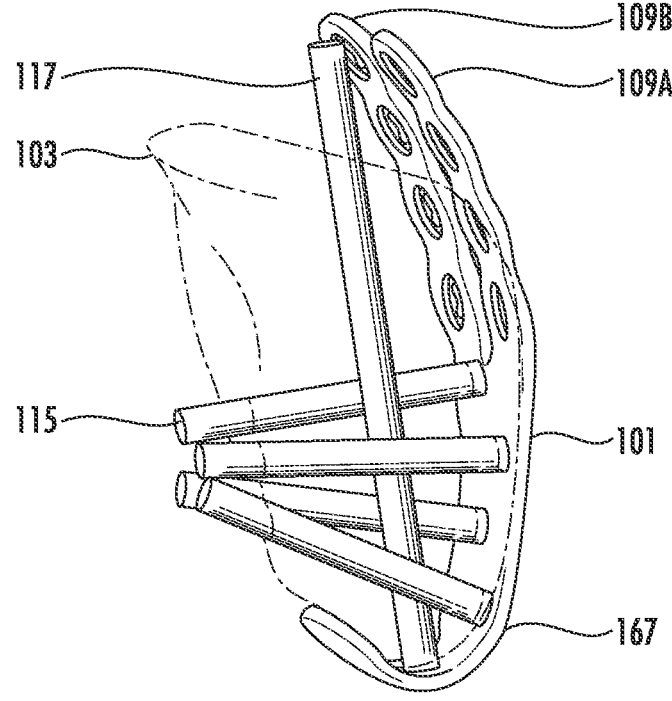
FIG. 5 is an additional side view of the dual-armed patella bone plate shown in FIG. 1, showing screw fixation angles.

Referring to FIGS. 3-6, a side view of the patella bone plate 101 on the patella 103 shows how hook 111 may be arranged under the apex 133 of patella 103, thereby securing the patella bone plate 101 to the patella 103. Distal fixation screw path 117 may allow for a bone screw to be inserted into the patella 103 from the apex 133 to the base 131. This feature allows for fracture reduction across almost the entirety of the patella 103. As can also be seen in FIG. 4, distal fixation screw path 117 may be parallel to, but offset from, the longitudinal axis 171 of contoured body 163. Additionally, since the distal fixation screw path 117 is located between contoured arms 109a and 109b and the openings 113 located on the contoured body 163, interference of distal fixation screw path 117 and the anterior fixation screw paths 115 may be minimized. The side view of the patella bone plate 101 illustrated in FIG. 5 shows various exemplary angles of the anterior fixation screw paths 115, allowing for various types of patella fractures to be more effectively treated. Although anterior fixation screw paths 115 are shown extending through patella 103, this is for illustrative purposes, as in actual use, the fixators may not extend through both sides of patella 103.

The curvature at the inferior end portion 167 of patella bone plate 101 is illustrated in FIGS. 5 and 6. As previously described, cutouts 125 allow for a surgeon to intra-operatively bend or more easily bend contoured arms 109a and 109b, as well as contoured body 163. However, patella bone plate 101 is also provided with hook 111, which may be provided pre-bent. This curvature allows hook 111 to slip behind a patient's patella 103, for example, and to rest on or otherwise be arranged adjacent to the distal posterior surface of the patella.

In some examples, hook 111 may include a distal hole 104. In various examples, hook may be located at, near, adjacent to, and/or the like a bottom end or distal-most point of patella bone plate 101. As previously described, when the patellar tendon 107 is split and hook 111 is placed on the patella 103, the arrangement of distal hole 104 may allow for a bone fixator to be placed through distal hole 104, for instance, and reach almost the entire proximal-to-distal length of patella 103

FIG. 6 also illustrates the varying curvatures of patella bone plate 101. In FIG. 6, R1 indicates a radius of curvature of the patella bone plate 101 from the superior end 173 to hook 111. Adjacent inferior end portion 167 to distal hole 104, patella bone plate 101 may be formed with a second radius of curvature R2 (i.e., the curvature of the hook 111). In some examples, radius of curvature R2 may be determined to be sufficient for hook 111 to correspond to the corresponding shape of the distal end of the patella 103, for instance, the apex 133. In various examples, R2 may correspond to a circle 161 having a radius, diameter, and/or circumference that corresponds to a shape allowing hook 111 to curve around the apex 111 and be directly adjacent, if not in contact, with the patella. In some examples, R2 may be about 0.5 mm, about 1 mm, about 3 mm, about 5 mm, about 7 mm, about 10 mm, about 15 mm, about 20 mm, and any value or range between any two of these values (including endpoints).

Figure 7:
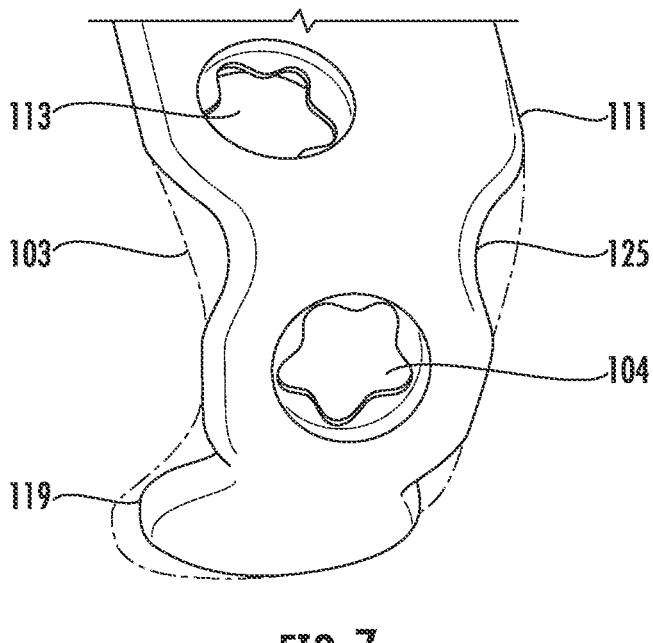
FIG. 7 is a perspective view of an inferior portion of the dual-armed patella bone plate shown in FIG. 1.
Figure 8:
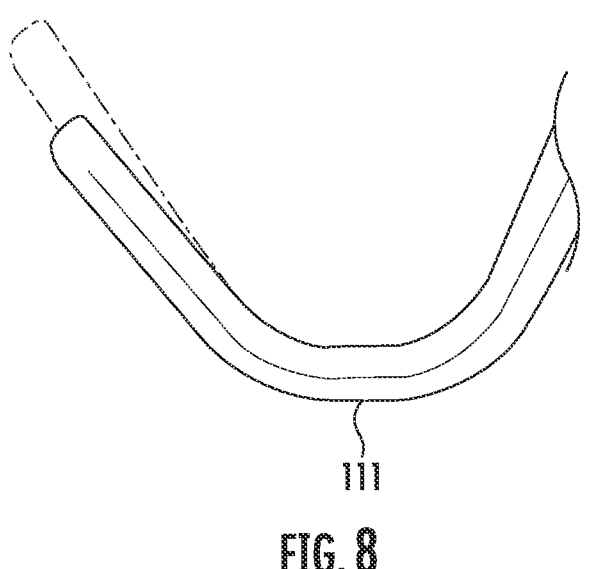
FIG. 8 is a side view of the dual-armed patella bone plate shown in FIG. 7.

Referring to FIGS. 7 and 8, the inferior end portion 167 of patella bone plate 101 may further include a paddle 119. Paddle 119 may be configured to extend, for example, up to the distance 162, in a superior direction from hook 111 and provides extra support to cup the posterior side of patella 103. FIG. 7 illustrates cutouts 125 at the inferior end portion 167 of patella bone plate 101. Cutouts 125 are notches or areas of the patella bone plate 101 between opening 113 and distal hole 104 where material has been removed from the sides of patella bone plate 101. The notches or removal of material makes the patella bone plate 101 easier to bend or contour. This allows the patella bone plate 101 to be contoured to more closely match a particular patient's anatomy.

A patella bone plate 101 may be implanted using various surgical techniques. For example, after the surgical site has been exposed, any fragments of patella 103 should be anatomically reduced, or drawn together prior to plate application and fixator insertion. Reduction aids such as K-wires may be placed into patella 103 fragments and/or reduction forceps may be used. These reduction aids should be placed so as not to interfere with final plate placement. In various examples, patella bone plate 101 may be positioned as desired along the superior portion of patella 103. Plate placement may be adjusted to achieve the best fit position on each individual patient. Patella bone plate 101 may be bent or contoured as needed by the surgeon to achieve a better fit to the anterior side of the patella. For example, any or all of paddle 119, contoured body 163, and/or contoured arms 190a and 109b may be bent to achieve an optimal fit. Fluoroscopy or other techniques may also be used to confirm patella bone plate 101 position.

In some examples, patella bone plate 101 may be provisionally fixed to patella 103, for instance, using K-Wires, reduction clamps, provisional fixation pins, and/or other devices. The patellar tendon may be split and hook 111 may be placed under the distal-most portion of the patella 103. The surgeon may proceed with fixator insertion as desired. Fluoroscopy o other techniques may be used to verify screw path placement during drilling of the screws in the plate to prevent joint penetration. Optionally, the patella bone plate 101 may be secured to the patella 103, for instance, at the apex of the patella 103 with one or more fasteners, such as a proximally extending bone screw.

Figure 9:
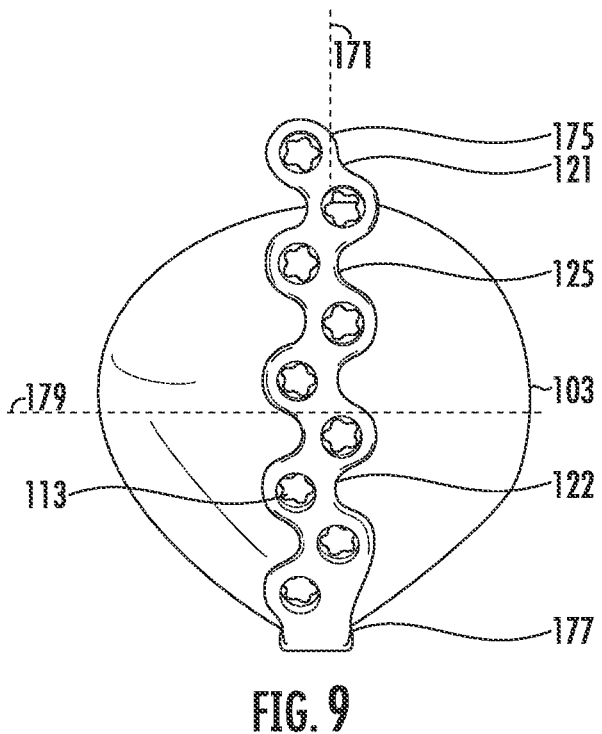
FIG. 9 is a front view of a single-armed or staggered patella bone plate on a patella in accordance with one or more features of the present disclosure.
Figure 10:
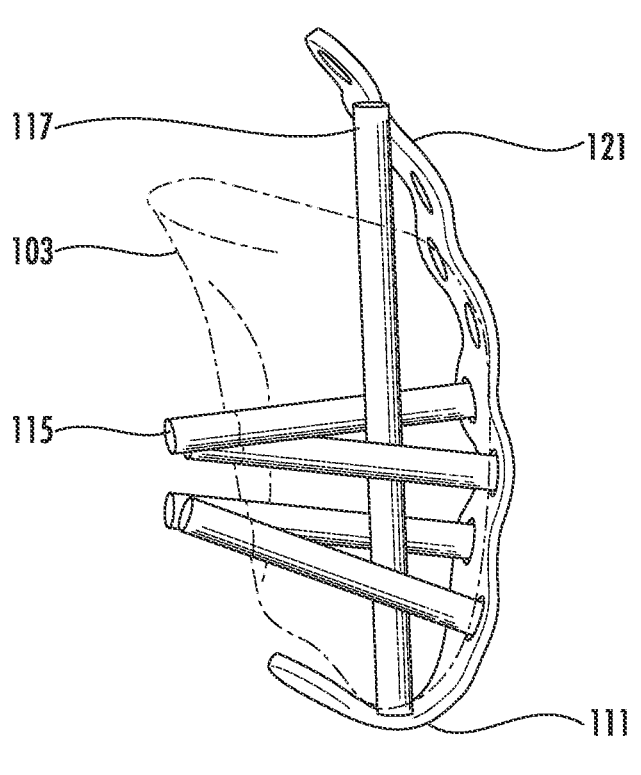
FIG. 10 is a side view of the staggered patella bone plate shown in FIG. 9, further illustrating screw fixation angles.
Figure 11:
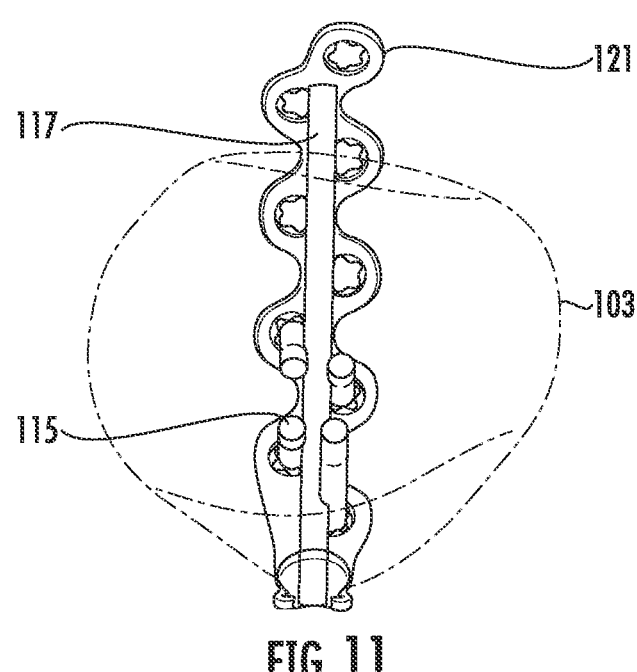
FIG. 11 is a rear view of the staggered patella bone plate shown in FIG. 9, further illustrating screw fixation angles.

FIGS. 9-12 illustrate some examples of a single-arm or staggered patella bone plate according to the present disclosure. FIG. 9 shows patella bone plate 121 mounted on a patella 103. Patella bone plate 121 has a contoured body 122 with a superior end portion 175 and an inferior end portion 177. Patella bone plate 121 also includes a plurality of openings 113 and cutouts 125 arranged along the patella bone plate 121. Openings 113 may be staggered along the length of the patella bone plate 121 and/or may be offset from longitudinal axis 171. In some examples, openings 113 may be offset from each other along a medial-lateral axis 179, for instance, such that openings 113 are diagonally opposed (e.g., catty-corner) from each other. Openings 113 on a given side of longitudinal axis 171 may also be separated by cutouts 125. In various examples, a distal fixation screw path 117 and anterior fixation screw paths 115 may be provided. Although anterior fixation screw paths 115 are shown extending through patella 103, in actual use, the fixators may not extend through both sides of patella 103. Distal fixation screw path 117 may be parallel to, and offset from, longitudinal axis 171.

The arrangement of openings 113 may allow for distal fixation screw path 117 and anterior fixation screw paths 115 to not interfere with each other when a surgeon is inserting fixators. In some examples, cutouts 125 may operate to reduce the cross-sectional area of the patella bone plate 121 and allow a surgeon to bend the plate intraoperatively. In various examples, a hook 111 may be provided with a distal hole 104, cutouts 125 and a distal paddle 119 extending in a superior direction from hook 111. Hook 111 may allow for patella bone plate 121 to be inserted behind the central distal portion of a patient's patella 103 and to rest on or otherwise be arranged adjacent to the distal inferior surface of the patella 103.

Figure 12:
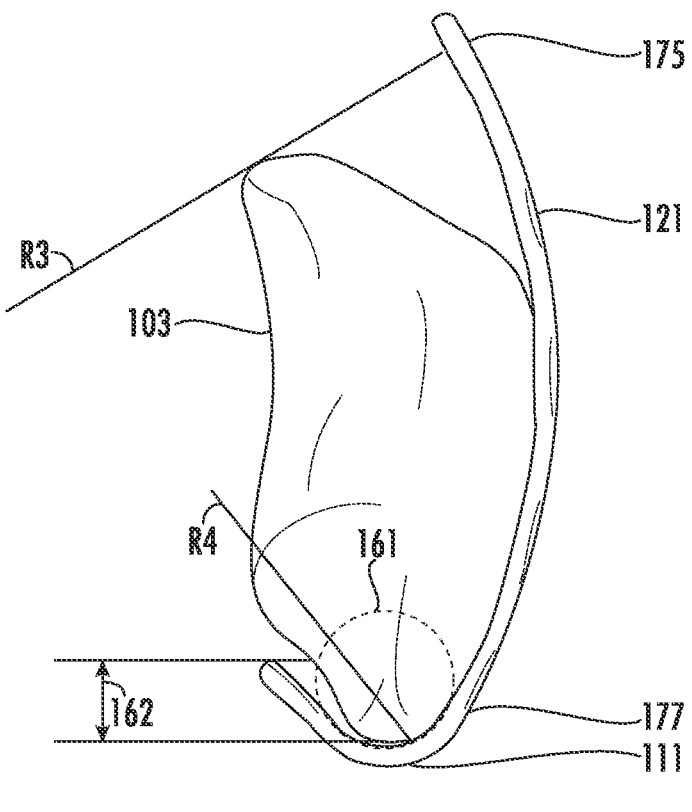
FIG. 12 is an additional side view of the staggered patella bone plate shown in FIG. 9, showing the radii of curvature of the patella bone plate.

FIG. 12 illustrates the varying curvatures of patella bone plate 121. In FIG. 12, R3 indicates a radius of curvature of the contoured body 122 from the superior end portion 175 to inferior end portion 177. From adjacent inferior end portion 177 to distal hole 181, patella bone plate 121 may be formed with a second radius of curvature R4 (i.e., the curvature of the hook 111).

Patella bone plate 121 may be implanted using various surgical techniques. For example, after the surgical site has been exposed, fragments of patella 103 should be anatomically reduced, or drawn together prior to plate application and fixator insertion. Reduction aids, such as K-wires, may be placed into patella 103 fragments and/or reduction forceps may be used. These reduction aids should be placed so as not to interfere with final plate placement.

In some examples, patella bone plate 121 may be positioned as desired along the superior portion of patella 103. Plate placement may be adjusted to achieve an optimal fit position on each individual patient. Patella bone plate 121 may be bent as needed by the surgeon to achieve an appropriate fit to the anterior side of the patella. For example, distal hook end 111 or contoured body 122 may be bent to achieve an appropriate fit. A tool, such as bending pliers (not shown), may be used to adjust the orientation of holes 113. Fluoroscopy or other techniques may be used to confirm patella bone plate 121 position. In various examples, the patella bone plate 121 may be provisionally fixed to patella 103 using various devices, for example, K-Wires, reduction clamps, provisional fixation pins, and/or the like. The patellar tendon may be split and hook 111 may be placed under the distal-most portion or end of the patella 103. The surgeon may proceed with fixator insertion as desired. Fluoroscopy or other techniques may be used to verify screw path placement during drilling of the screws in the patella bone plate 121 to prevent joint penetration. Optionally, patella bone plate 121 may be secured at the apex of the patella 103, for example, with a proximally extending bone fastener (e.g., screw).

Figure 13:
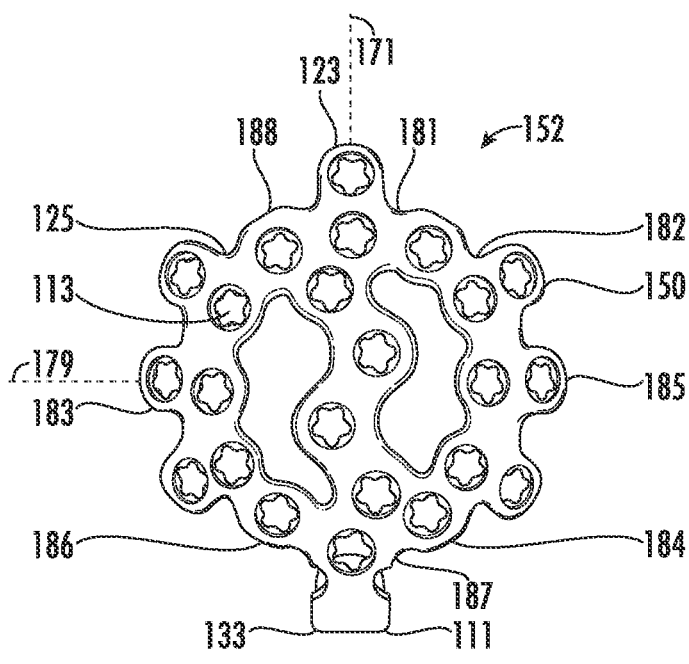
FIG. 13 is a front view of a first example of a meshed patella bone plate with a hook in accordance with one or more features of the present disclosure.
Figure 14:
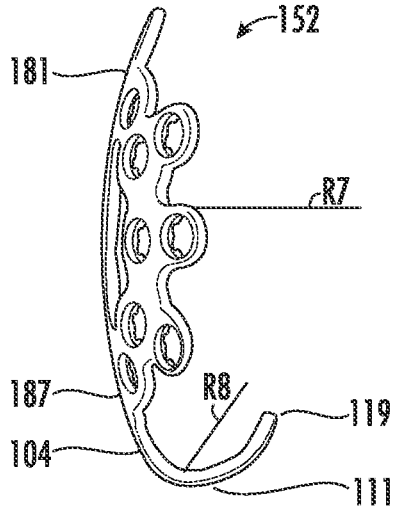
FIG. 14 is a side view of the meshed patella bone plate shown in FIG. 13.

FIGS. 13 and 14 illustrate an example of a meshed patella bone plate (or mesh) 152. Mesh 152 is similar to the examples shown in FIGS. 9-12 in that it has a staggered patella bone plate 123, but it is also formed with a peripheral portion 150. In various examples, mesh 152 may be monolithically, integrally, or otherwise formed with a peripheral portion 150. Peripheral portion 150 may also be coupled to a patella bone plate 123 by welding, fastener (e.g., screw) fixation, mechanical fixation or any other means contemplated in the art. As in the example shown in FIGS. 9-12, openings 113 may be staggered along the length of the patella bone plate 123 and offset from longitudinal axis 171. Furthermore, openings 113 may be offset from each other along medial-lateral axis 179, with the result being that openings 113 may be diagonally opposed (e.g., catty-corner).

In various examples, peripheral portion 150 may be further composed of four segments; medial-superior segment 182, medial-inferior segment 184, lateral-inferior segment 186 and lateral-superior segment 188. In some examples, medial-superior segment 182 may meet medial-inferior segment 184 at medial end 185 and lateral-superior 188 may meet lateral-inferior segment 186 at lateral end 183. Medial-superior segment 182 may meet lateral-superior segment 188 at superior end 181 and medial-inferior segment 184 may meet lateral-inferior segment 186 at inferior end 187.

In some examples, openings 113 may be provided along any or all of the segments and/or medial/lateral ends 185 and 183, respectively. Peripheral portion 150 may also be provided with a radius of curvature R7, like patella bone plate 121. In various examples, mesh 152 may include additional screw fixation holes 113 adjacent medial end 185 and lateral end 183. In various examples, for instance, mesh 152 may also include one fewer screw fixation hole 113 adjacent superior end 181.

Figure 15:
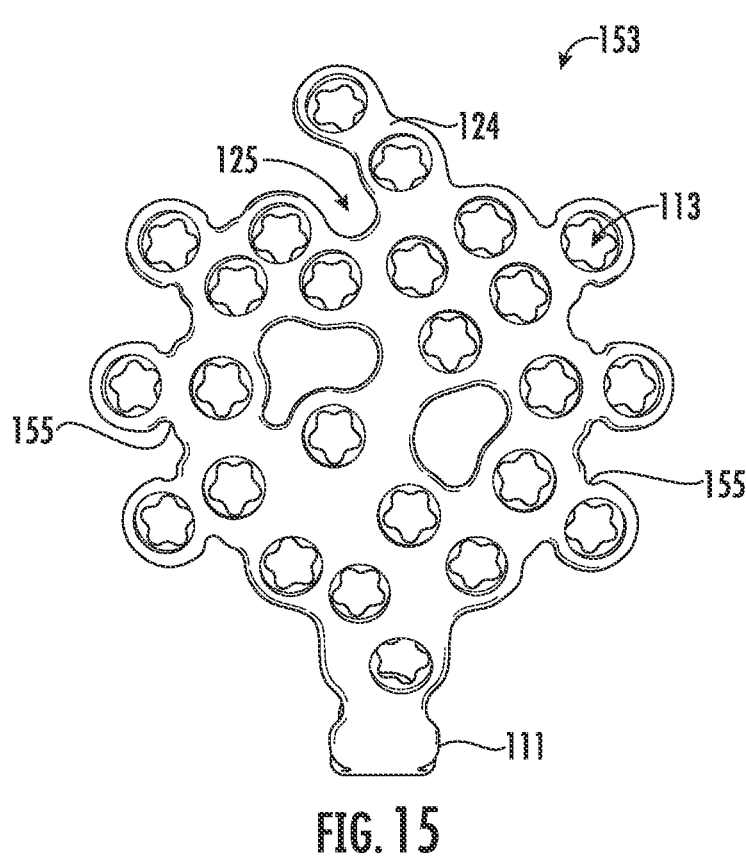
FIG. 15 is a front view of a second example of a meshed patella bone plate with a hook in accordance with one or more features of the present disclosure.
Figure 16:
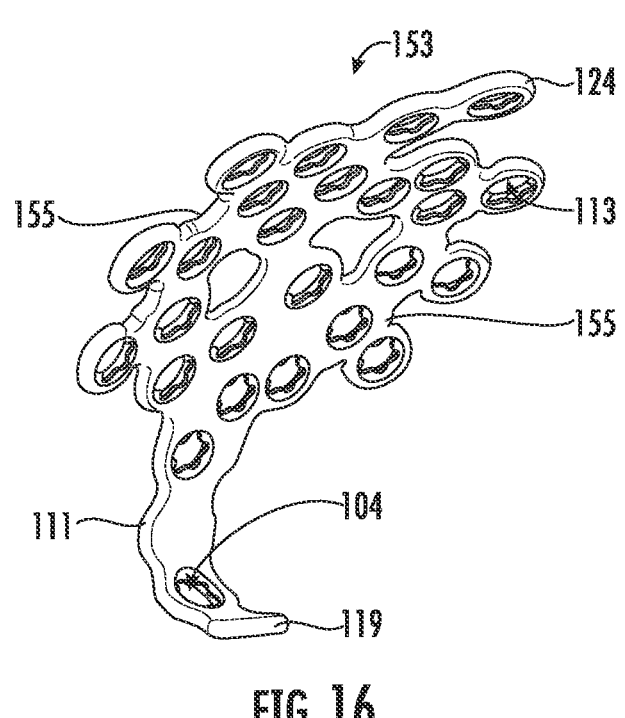
FIG. 16 is a back view of the meshed patella bone plate shown in FIG. 15

FIGS. 15 and 16 illustrate an example of a meshed patella bone plate (or mesh) 153. More specifically, FIG. 15 depicts a front view of mesh 153 with a patella bone plate 124 coupled or formed with peripheral portion 155 and FIG. 16 depicts a back view of mesh 153.

Figure 17:
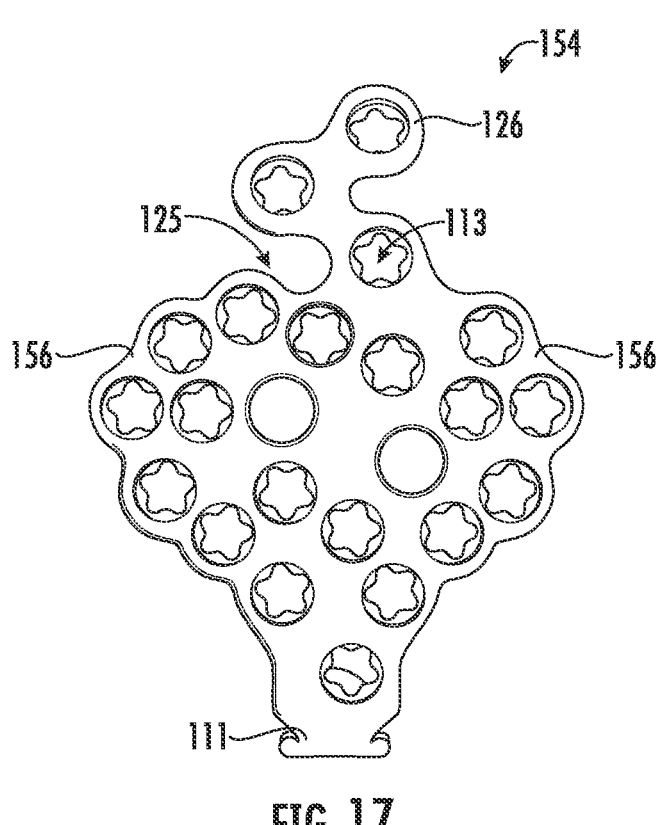
FIG. 17 is a front view of a third example of a meshed patella bone plate with a hook in accordance with one or more features of the present disclosure.
Figure 18:
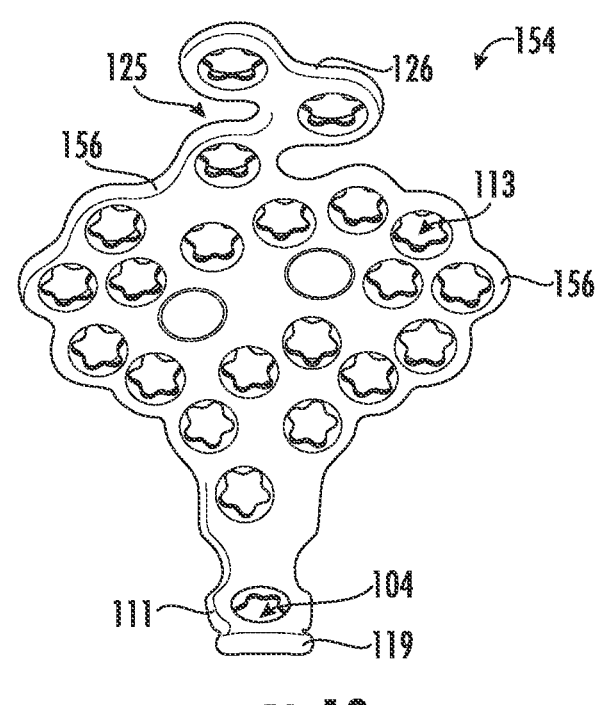
FIG. 18 is a back view of the meshed patella bone plate shown in FIG. 17.

FIGS. 17 and 18 illustrate an example of a meshed patella bone plate (or mesh) 154. More specifically, FIG. 17 depicts a front view of mesh 154 with a patella bone plate 126 coupled or formed with peripheral portion 156 and FIG. 18 depicts a back view of mesh 154.

Meshes 152-154 may be configured to cover a portion or area of the anterior surface of the patella. For example, one or more of mesh 151-154 may cover about 10%, about 20%, about 30%, about 50%, about 60%, about 70%, about 80%, about 90%, or any value or range between any two of these values (including endpoints).

As in the previous examples, a distal fixation screw path and anterior fixation screw paths are provided for mesh plates 152-154. Distal fixation screw path may be parallel to and/or offset from longitudinal axis 171. The arrangement of openings 113 allows for distal fixation screw path and anterior fixation screw paths to not interfere with each other when a surgeon is inserting fixators. In various examples, cutouts 125 may operate to reduce the cross-sectional area of the patella bone plate 121, 123, 124, and 126 and allow a surgeon to bend the plate intraoperatively. Also as in the previous example, a hook 111 may be provided with a distal hole 104, cutouts 125 and a distal paddle 119. The hook 111 may allow for a patella bone plate 121,123, 124, 126 to be inserted behind the distal portion or end of a patient's patella and to rest on or otherwise be arranged adjacent to the distal inferior surface of the patella 103. As in the previous examples, adjacent inferior end portion 177 to distal hole 104, patella bone plate 121,123, 124, 126 may be formed with a radius of curvature, for instance, the same as or similar to R8. Meshes 152-154 may be of particular advantage for complex fractures of the patella where additional fixation locations and trajectories are needed.

In some examples, a mesh may be formed of any combination of a patella bone plate (for instance, the same or similar to 101, 121, 123, and/or 124) and peripheral portions (for instance, the same or similar to 150, 153, and/or 154) according to the present disclosure.

A meshed patella bone plate, for example, including meshes 152-153 may be implanted using various techniques. For example, after the surgical site has been exposed, any fragments of patella 103 may be anatomically reduced and/or drawn together prior to plate application and fixator insertion. Reduction aids such as K-wires may be placed into patella 103 fragments and/or reduction forceps may be used. These reduction aids may be placed so as not to interfere with final plate placement. In various examples, the meshed patella bone plate may be positioned as desired along the superior portion of patella 103. Meshed patella bone plate placement may be adjusted to achieve an appropriate or optimal fit position on each individual patient. Fluoroscopy or other techniques may be used to confirm plate position. In some examples, the meshed patella bone plate may be provisionally fixed to patella 103, for instance, using K-Wires, reduction clamps, provisional fixation pins, and/or the like. The patellar tendon may be split and the hook 111 placed under the distal-most portion of the patella 103. The surgeon may proceed with fixator insertion as desired. Fluoroscopy or other techniques may be used to verify screw path placement during drilling of the screws in the plate to prevent joint penetration. Optionally, the meshed patella bone plate may be secured at the apex of the patella with a proximally extending bone screw.

As generally shown, and as will be appreciated by one of ordinary skill in the art, the number of undercuts, variable angled openings, locking screw openings, etc. will be variable between the various bone fixation plates depending on various factors. Non-limiting examples of such factors may include the length of the patella bone plate, the width of the patella bone plate, patella condition, surgeon preference, and/or the like.

The foregoing description has broad application. Accordingly, the discussion of any example is meant only to be explanatory and is not intended to suggest that the scope of the disclosure, including the claims, is limited to these examples. In other words, while illustrative examples of the disclosure have been described in detail herein, it is to be understood that the inventive concepts may be otherwise variously embodied and employed, and that the appended claims are intended to be construed to include such variations, except as limited by the prior art.

The term "a" or "an" entity, as used herein, refers to one or more of that entity. As such, the terms "a" (or "an"), "one or more" and "at least one" can be used interchangeably herein. The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein. The phrases "at least one", "one or more", and "and/or", as used herein, are open-ended expressions that are both conjunctive and disjunctive in operation.

All directional references (e.g., proximal, distal, upper, underside, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

What is claimed is:

1. A patella bone plate, comprising:
   an elongated contoured body configured to extend along
   a longitudinal axis of at least a portion of an anterior portion of a patella, the longitudinal axis extending from a base to an apex of the patella, the contoured body including a plurality of openings arranged and configured to receive fasteners for coupling the patella bone plate to the patella; and a hook portion configured to be arranged around the apex of the patella and extending a distance along a posterior portion of the patella, the hook portion including a distal opening arranged and configured to receive a distal fastener for coupling the patella bone plate to a distal end of the patella;

wherein the plurality of openings formed in the contoured body are arranged in a staggered pattern; and wherein the contoured body comprises a pair of parallel contoured arms extending from a superior portion of the elongated contoured body.

2. The patella bone plate of claim 1, wherein the distal opening provides a fixation screw path for the distal fastener from the apex towards the base of the patella.

3. The patella bone plate of claim 2, wherein the fixation screw path is offset from a longitudinal axis of the contoured body.

4. The patella bone plate of claim 2, wherein the fixation screw path is configured to allow the distal fastener to avoid interference from body fasteners configured to couple at least a portion of the contoured body to the patella.

5. The patella bone plate of claim 1, wherein the distance along the inferior portion of the patella is about 1 mm to about 10 mm.

6. The patella bone plate of claim 1, wherein the contoured body has a radius of curvature corresponding to a radius of curvature of the anterior portion of a patella.

7. The patella bone plate of claim 1, wherein the hook portion has a radius of curvature corresponding to at least a portion of a radius of curvature of the apex.

8. The patella bone plate of claim 1, wherein the hook portion has a radius of curvature configured to allow the hook portion to extend around the axis and contact the posterior portion of the patella.

9. The patella bone plate of claim 1, wherein the hook portion is configured to be inserted through a split patellar tendon of the patella.

10. The patella bone plate of claim 1, further comprising a peripheral portion coupled to the contoured body to form a mesh.

11. The patella bone plate of claim 10, further comprising a plurality of openings in the mesh configured to receive fasteners for coupling the mesh to the anterior portion of the patella, the plurality of openings comprising about 15 openings to about 25 openings.

12. The patella bone plate of claim 10, wherein the mesh is configured to cover about 30% to about 50% of an area of the anterior portion.

13. The patella bone plate of claim 10, wherein the mesh comprises a medial-superior segment, a medial-inferior segment, a lateral-inferior segment, and a lateral-superior segment.

14. The patella bone plate of claim 1, wherein the elongated contoured body includes a length extending parallel to the longitudinal axis and a width extending perpendicular to the longitudinal axis, the length being greater than the width.

15. A method of treating a patella fracture using a patella bone plate, the method comprising:

implanting the patella bone plate on the patella via:

arranging an elongated contoured body of the patella adjacent to an anterior portion of the patella, the contoured body configured to extend along a longitudinal axis of at least a portion of an anterior portion of a patella, the longitudinal axis extending from a base to an apex of the patella, the contoured body including a plurality of openings arranged in a staggered pattern, the plurality of openings arranged and configured to receive fasteners for coupling the patella bone plate to the patella, the contoured body comprises a pair of parallel contoured arms extending from a superior portion of the elongated contoured body; and arranging a hook portion of the patella bone plate around an axis of the patella, the hook portion configured to be arranged around the apex of the patella and extend a distance along a posterior portion of the patella, the hook portion including a distal opening arranged and configured to receive a distal fastener for coupling the patella bone plate to a distal end of the patella.

16. The method of claim 15, further comprising:

splitting the patellar tendon of the patella; and inserting the hook portion through a split patellar tendon.

17. The method of claim 15, further comprising:

inserting a distal fastener through the distal opening arranged in the hook portion, the distal fastener extending along a fixation screw path from the apex towards the base of the patella.

18. The method of claim 17, wherein the fixation screw path is offset from the longitudinal axis of the contoured body.

19. The method of claim 17, further comprising:

inserting one or more fasteners through the plurality of openings formed in the contoured body for coupling the patella bone plate to a portion of the patella;

wherein the fixation screw path is configured to allow the distal fastener to avoid interference with the one or more fasteners.

* * * * *